US010343807B2

(12) United States Patent
Mäkiranta

(10) Patent No.: US 10,343,807 B2
(45) Date of Patent: Jul. 9, 2019

(54) EMPTYING DEVICE, ASSEMBLY, AND METHOD FOR EMPTYING SUCTION BAG

(71) Applicant: Serres Oy, Kauhajiko as. (FI)

(72) Inventor: Jarmo Mäkiranta, Kauhajoki as (FI)

(73) Assignee: Serres Oy, Kauhajoki as. (FI)

( * ) Notice: Subject to any disclaimer, the term of this patent is extended or adjusted under 35 U.S.C. 154(b) by 331 days.

(21) Appl. No.: 15/029,134

(22) PCT Filed: Oct. 15, 2014

(86) PCT No.: PCT/FI2014/050780
§ 371 (c)(1),
(2) Date: Apr. 13, 2016

(87) PCT Pub. No.: WO2015/055893
PCT Pub. Date: Apr. 23, 2015

(65) Prior Publication Data
US 2016/0257439 A1 Sep. 8, 2016

(30) Foreign Application Priority Data
Oct. 16, 2013 (FI) .................................... 20136025

(51) Int. Cl.
*B65B 69/00* (2006.01)
*A61M 1/00* (2006.01)

(52) U.S. Cl.
CPC ........ *B65B 69/0041* (2013.01); *B65B 69/005* (2013.01); *B65B 69/0016* (2013.01); *A61M 1/0005* (2013.01); *A61M 1/0017* (2014.02)

(58) Field of Classification Search
CPC ........... B65B 69/0008; B65B 69/0016; B65B 69/0041; B65B 69/005; B65B 69/0033;
(Continued)

(56) References Cited

U.S. PATENT DOCUMENTS 4,111,204 A * 9/1978 Hessel ................ A61M 1/0001
604/321
4,166,481 A 9/1979 Farris
(Continued)

FOREIGN PATENT DOCUMENTS

DE 19514467 A1 10/1996
DE 19856378 A1 6/2000
(Continued)

OTHER PUBLICATIONS

Australian Examination Report for Application No. 2014336011 dated Aug. 21, 2017, 3 pages.
(Continued)

*Primary Examiner* — Glenn F Myers
(74) *Attorney, Agent, or Firm* — Seyfarth Shaw LLP

(57) ABSTRACT

The invention relates to a suction bag emptying device (13) comprising a container (15) with a lid for a suction bag to be placed into the container. The container (15) has a discharge point (17) for removal of the contents of the suction bag. The emptying device (13) is provided with a holder for suspending a suction bag with a lid from the holder by the lid, and a jacket (24) for lateral support of the suction bag. The lid (14) of the emptying device (13) is provided with means for puncturing the lid (4) of the suction bag (3) and for supplying pressurized liquid or gas into the suction bag (3). The invention also relates to an assembly comprising at least one suction bag (3) and a suction bag emptying device (13), and to a method for emptying the suction bag (3).

7 Claims, 6 Drawing Sheets

20
19
16
14
21
18
15
24
13
3
22
17

(58) Field of Classification Search
CPC .............. A61M 1/0017; A61M 1/0005; A61M 1/0023; A61M 1/0084; A61M 1/0088; A61M 1/0001; A61M 1/0007; A61M 1/0021; B67B 7/24; B67B 7/26; B67B 7/28
See application file for complete search history.

(56) References Cited

U.S. PATENT DOCUMENTS

| | | | | |
|---|---|---|---|---|
| 4,961,440 | A * | 10/1990 | Wright | B08B 9/093 134/167 R |
| 6,652,495 | B1 | 11/2003 | Walker | |
| 6,808,515 | B2 * | 10/2004 | Takahashi | A61M 1/0001 137/571 |
| 9,700,171 | B2 * | 7/2017 | Hanneson | A47J 31/46 |
| 2004/0079404 | A1 * | 4/2004 | Burrows | A61L 11/00 134/200 |
| 2012/0048080 | A1 | 3/2012 | Zardini | |

FOREIGN PATENT DOCUMENTS

| | | | |
|---|---|---|---|
| GB | 2136384 | A | 9/1984 |
| WO | 8302722 | A1 | 8/1983 |
| WO | 02/074632 | A1 | 9/2002 |
| WO | 2010/128377 | A2 | 11/2010 |

OTHER PUBLICATIONS

Patentti-Ja Rekisterihallitus Finland Search Report dated Jun. 13, 2014; 1 page.
Patentti-Ja Rekisterihallitus Findland Office Action dated Jun. 13, 2014; 5 pages.
PCT International Search Report on Patentability, dated Nov. 25, 2015; 11 pages.
Chinese Office Action for Application No. 201480056625.8 dated Dec. 14, 2016, 15 pages.

* cited by examiner

EMPTYING DEVICE, ASSEMBLY, AND METHOD FOR EMPTYING SUCTION BAG

CROSS REFERENCE TO RELATED APPLICATIONS

The present application is a national stage application of PCT/FI2014/050780, filed Oct. 15, 2014, and claims priority to Finland patent application 20136025, filed Oct. 16, 2013, the disclosures of which are incorporated herein by reference.

BACKGROUND OF THE INVENTION

The invention relates to a suction bag emptying device comprising a container with a lid for a suction bag to be placed into the container, the container having a discharge point for the removal of the contents of the suction bag.

The invention also relates to an assembly comprising at least one suction bag and a suction bag emptying device, and to a method for emptying a suction bag.

Publication U.S. Pat. No. 3,809,577 discloses a device provided with a lid and scissor- or knife-type members that cut open the bottom of the suction bag. Suction bags are placed into the device in a basket and the lid is closed, the basket being thus pressed down towards the scissor- or knife-type members that cut open the suction bags. The closing of the lid of the device also activates a rinsing process in which the suction bags are rinsed and disinfected.

A problem with the device of the above publication is that, firstly, its structure is complicated. Secondly, it is not certain that the suction bag could be emptied completely, or that the inside of the suction bag would be rinsed throughout, because the rinsing takes place from outside of the suction bags. Thirdly, the suction bags are cut in an uncontrollable manner at the point where they are within reach of the scissor- or knife-type members.

BRIEF DESCRIPTION OF THE INVENTION

An emptying device of the invention offers an improvement on the above problems. The emptying device of the invention is characterized in that the emptying device has a holder for suspending the suction bag provided with a lid from the holder by the lid and a jacket for lateral support of the suction bag, the lid of the emptying device being provided with means for puncturing the lid of the bag and for supplying pressurized liquid or gas into the bag to be emptied.

The structure of the emptying device is simple and hence the device is reliable and maintenance-free. The suction bag is emptied completely, its inside can be rinsed and, when necessary, disinfected more reliably than with prior art methods. The contents of the bag are emptied in a controlled manner from one and the same point at the lower part of the bag, the rising thus reaching all parts of the suction bag and no pockets containing body fluids are left in the bag. Significant savings in waste costs are made when all that needs to be disposed of is the empty suction bag, which is taken to incineration, for example, for disposal.

A further advantage of the emptying device of the invention is that the device can be used for emptying suction bags of different lengths if the outer diameter of the bags is substantially equal. The device may also be constructed without sharp parts that a person emptying the bag might hit. The person emptying the bag is also well protected against any splatters because the suction bag lid sets tightly against the emptying device so that contents of the bag cannot splash upwards even if the lid of the emptying device were opened for some reason.

Although the emptying device is particularly suitable for suction bags, the emptying device may also be used to handle bags containing other body fluids. Suction bags are used in hospitals or other facilities performing medical operations, such as surgery. The emptying device of the invention may be used for handling a suction bag such as the one described below:

The suction bag usually comprises a bag portion and a lid fixedly fastened to the bag portion. The bag portion is made of a flexible plastic material, such as polyethylene. The bag portion is formed of a tubular plastic film. One end of the tubular plastic film is closed by sealing the edges of the plastic film together, while at its other end the tubular plastic film is fixedly fastened to the lid. Also the lid is made of a polyolefin plastic material, such as polyethylene or polypropylene, but it is stiffer than the bag portion. The lid is a substantially uniform piece. The lid has a patient fitting to which a hose delivering fluid from the patient is coupled. The lid also has a channel for transmitting negative pressure and a filter for preventing impurities from entering the suction system. The filter is usually fastened to an inner surface side of the suction bag lid, although it may also be located elsewhere in association with the channel.

The suction bag is used with a collection reservoir whose one end is open, and together they form a suction bag arrangement. The bag portion of the suction bag is placed inside the collection reservoir, the suction bag lid closing the collection reservoir. The collection reservoir is provided with a fitting that has a flow connection to a source of negative pressure for generating a negative pressure between the inner surface of the collection reservoir and the outer surface of the suction bag. The lid is provided with a channel for transmitting the negative pressure from a space between the inner surface of the collection reservoir and the lid to the inner part of the suction bag.

The details of the suction bag suitable for handling in the emptying device may vary from those disclosed above. Usually, however, the bag has a flexible bag portion and a stiffer lid fixedly fastened thereto.

In the following, the structure and operation of the bag are described. The emptying device described is in its operating position.

The bag emptying device comprises a container with a lid for a bag to be placed into the container. The bag is placed to a holder in the container. A simplest form of the holder is the edge of the container on which the edge of the suction bag lid sets. Alternatively, the holder may be a shoulder or other arrangement provided in the container and suitable for suspending the bag. The shoulder is formed of an annular piece at the mouth of the container, the inner rim of the piece bordering on an outer wall of the jacket of the emptying device. In addition, also at least one suction bag suspension device may be provided on the suction bag lid or in association with it, a corresponding holder being provided in the emptying device. The jacket may form the inner wall of the container jacket especially when the emptying device is to be used for handling only one bag at a time. When the emptying device has a plural number of positions for bags to be emptied, a separate jacket is provided for each position. The rim of the suction bag lid rests on the shoulder, or the like, and the bag portion of the bag hangs downward.

The container has a discharge point for removal of the suction bag contents. The lid of the emptying device is provided with means for puncturing the suction bag lid and for supplying pressurized liquid or gas into the bag to be emptied.

The means for puncturing the lid of the bag and for supplying the pressurized fluid or gas into the bag to be emptied may be implemented in various ways. For example, the means may consist of a hollow cone with a blunt end or a hollow cylinder with a cutting edge or a hollow cone with a fixed pointed end. With the above means the suction bag lid may be punctured. The means have openings through which the fluid or gas may flow after the suction bag lid has been punctured. The above are naturally only examples of how the means in question may be implemented. In practice, the means for puncturing the lid of the bag and for supplying pressurized liquid or gas into the bag to be emptied may consist of one or more parts, but they are used for performing two functions: puncturing the lid of the bag and supplying pressurized liquid or gas into the bag. On the outer surface of the lid there is/are naturally a fitting/fittings for coupling the emptying device to a liquid or gas source, the fittings in turn being connected to the means for puncturing the lid of the bag and for supplying pressurized fluid or gas into the bag to be emptied.

When the suction bag is emptied, it is placed into the emptying device so that the rim of the lid sets against the holder. The holder may be an annular shoulder around the outside of the jacket, for example. It is also possible that the container mouth alone forms the necessary holder. The container is preferably dimensioned so that its height from the bottom to the holder is greater than the length of the suction bag. The suction bag length refers to a measure from the suction bag lid to the bottom of the bag. When the suction bag is shorter than the container height from the bottom of the container to the holder, the bottom of the bag never touches the bottom of the container. In other words, the bag hangs from the holder, such as a shoulder, by the rims of its lid.

When the bag is in place inside the container, the cover of the emptying device is closed. The means for puncturing the lid of the bag then puncture the lid. The means for supplying pressurized liquid or gas into the bag to be emptied are arranged to activate once the lid has been punctured. In other words, when the channel/channels carrying the liquid or gas have penetrated the suction bag lid, liquid or gas starts to flow into the suction bag.

The source of the pressurized gas or liquid may be a water supply network or a compressed air network. The source of pressurized gas or liquid may also be used for supplying disinfectants or sterilizers. The opening of the source of the pressurized gas or liquid may be connected to the closing of the lid so that the closing automatically starts the gas or liquid flow into the bag to be emptied. In its simplest form the opening of the gas or liquid source may take place manually, for example by opening a water tap.

As the pressurized gas or liquid starts to flow through the suction bag lid, pressure from the inside of the bag starts to act on the bag. The suction bag is laterally supported by a jacket, which may be the inner wall of the container or some other jacket surrounding the side of the bag close to its outer wall so that there is no possibility for the bag under pressure to bulge from the area protected by the jacket. The material of the suction bag thus begins to bulge at the bottom part of the bag, next to the seam, the bulging causing the bag to burst. The contents of the bag then flow out of the bag. The container has a discharge point through which the contents of the bag is arranged to exit. The discharge point may be an opening in the jacket or the bottom, for example, and in principle even the entire bottom of the container may be open when the emptying device is placed into a wash basin with a sewer, for example. It is also possible that the liquid exiting through the discharge point is guided into a closed container for further processing, or the fluid exiting through the discharge point is sterilized before it is allowed to flow into the sewer.

There may be at least one guide surface inside the jacket to guide the flow towards the discharge point. The gas or liquid flow rinses the inside of the bag. The bag is thus completely emptied, and the rinsing ensures that the inside of the bag is cleaned. When the hole is punctured in a controlled manner to the bottom part of the suction bag, pressurized gas or liquid flows through the entire bag and no pockets with body fluids left in them are formed in the bag.

After the rinsing has continued for a sufficient amount of time, the gas or liquid flow is cut off or the flow shuts off automatically e.g. when the cover of the emptying device is opened or a pre-set rinsing time expires. The rinsed bag may then be removed from the emptying device and taken to waste disposal.

The emptying device may be constructed in a number of ways. The emptying device may be a device meant for handling only one bag at a time, as disclosed below with reference to FIGS. 3 to 6. When the emptying device has one position for the bag to be emptied, the jacket supporting the bag laterally may consist of the inner wall of the container. The emptying device may be provided with several positions for placing more than one suction bag at a time into the device. When the emptying device has more than one position for the bags to be emptied, the jacket supporting the bag laterally may be a separate structural part inside the container.

The device may be provided with a uniform lid that has a plurality of means for puncturing the suction bag lid and for supplying pressurized gas or liquid into the suction bag to be emptied. Closing of the lid of the emptying device thus allows lids of a plural number of bags to be punctured and thus emptying and rinsing of the plural number of bags may be started simultaneously. The emptying device may also be provided with a plural number of positions for placing a plural number of bags into the device at a time so that the emptying device has a separate lid of each bag, the lid being provided with means for puncturing the lid of the bag and for supplying pressurized gas or liquid into the bag to be emptied. This type of arrangement enables a plural number of bags to be emptied and rinsed simultaneously so that when the first bag is in place, the lid may be closed to start the emptying and the rinsing immediately, while the filling of the other positions may be continued at the same time.

The suction bags and the emptying device are preferably used as a mutually compatible assembly. In other words, the emptying device is dimensioned to correspond to a specific suction bag/specific suction bags. This brings out the advantages of the emptying device still better.

BRIEF DESCRIPTION OF THE FIGURES

The invention is now described in closer detail in connection with preferred embodiments and with reference to the accompanying drawings, in which.

DETAILED DESCRIPTION OF THE INVENTION

Figure 1:
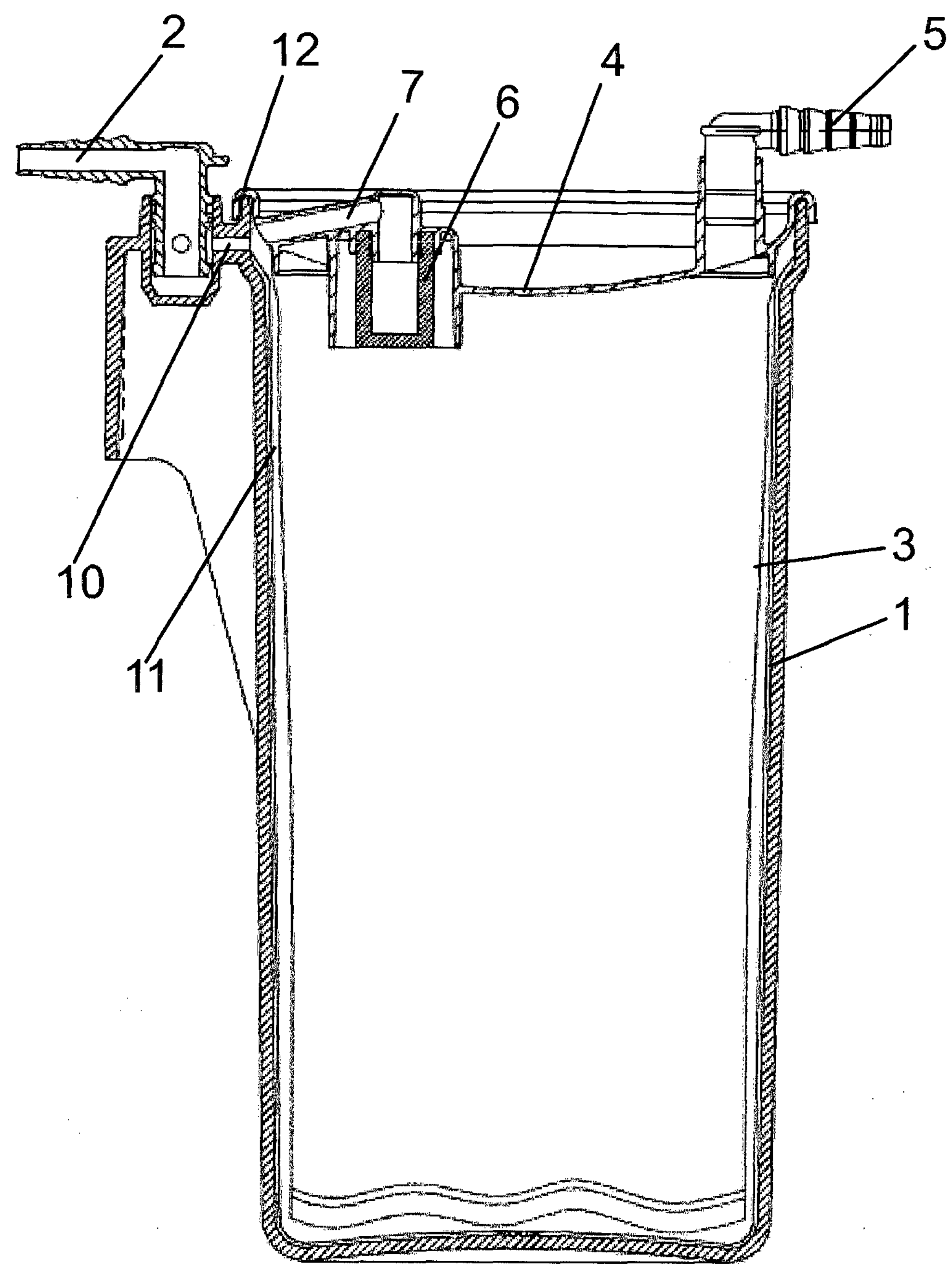
FIG. 1 is a side view of a suction bag arrangement.
Figure 2:
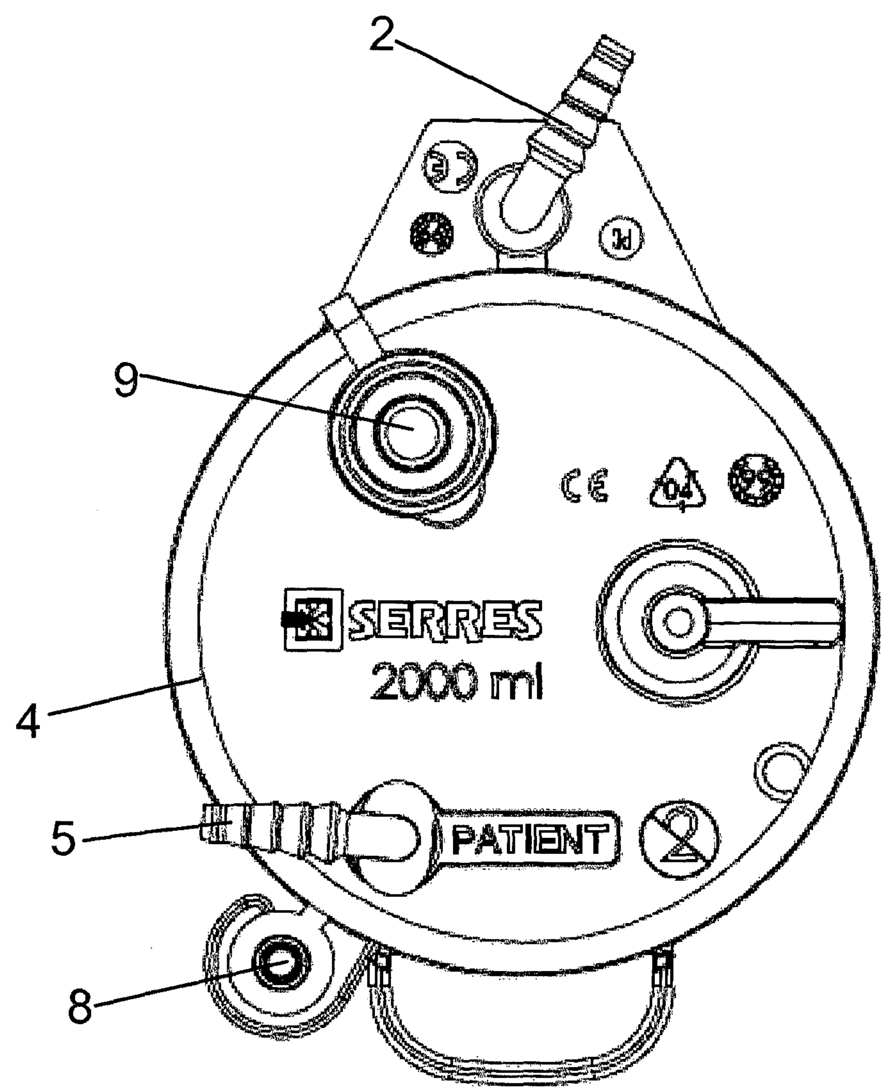
FIG. 2 is a top view of the suction bag arrangement of FIG. 1.

FIGS. 1 and 2 first disclose a structure and operation of a suction bag 3. The suction bag of FIGS. 1 and 2 is an example of a suction bag suitable to be emptied by an emptying device of the invention.

In accordance with what is shown in FIG. 1, the suction bag arrangement comprises a collection reservoir 1 that is open at one end, a suction bag 3 that may be arranged to the collection reservoir 1 and comprises a flexible bag portion that is fixedly fastened to a lid 4. The collection reservoir 1 is provided with a fitting 2, which is in a flow connection to a source of negative pressure, and a channel 10 for producing a negative pressure in an area 11 between an inner surface of the collection reservoir 1 and an outer surface of the suction bag 3. The lid 4 is provided with a patient fitting 5 for connecting a patient hose for fluid to the inner part of the suction bag 3, and the lid 4 has a channel 7 for transmitting negative pressure from a space between the inner surface of the collection reservoir 1 and the lid 4 into the inner part of the suction bag 3 and a filter 6 for preventing impurities from entering the suction system. The filter 6 is fastened to the lid surface on the inner side of the suction bag 3, and the lid 4 is a uniform piece.

FIG. 2 is a top view of the suction bag arrangement. In addition to the parts disclosed with reference to FIG. 1, FIG. 2 shows a plug 8 integrated in the lid 4 for closing the patient fitting 5 after use, and a fitting 9 used for connecting suction bag arrangements in series, for taking samples and for emptying.

An emptying device of the invention is shown in FIGS. 3 to 6. The emptying device 13 comprises a container 15 provided with a lid 14. The lid 14 is usually hinged to the container 15. The container 15 has a holder, in this case a shoulder 16, and a discharge point 17. The lid 14 is provided with means for puncturing the suction bag lid and for supplying pressurized liquid or gas into the suction bag to be emptied. In the case of FIGS. 3 to 6, the above-mentioned means are formed by a hollow cylinder 19 provided with a blunt conical head 18. The cylinder 19 has openings 21 through which the pressurized liquid or gas flows into the suction bag 3. The means for puncturing the suction bag lid and for supplying the pressurized liquid or gas into the suction bag to be emptied can be implemented in various other ways, too. Instead of the hollow cylinder 19 with a blunt conical head 18, a hollow cylinder with a cutting edge, for example, may be used, or a cone with a fixed pointed head that punctures the lid 4 of the suction bag 3, openings being provided on the cone above the pointed head to allow liquid or gas to flow 18.

Figure 3:
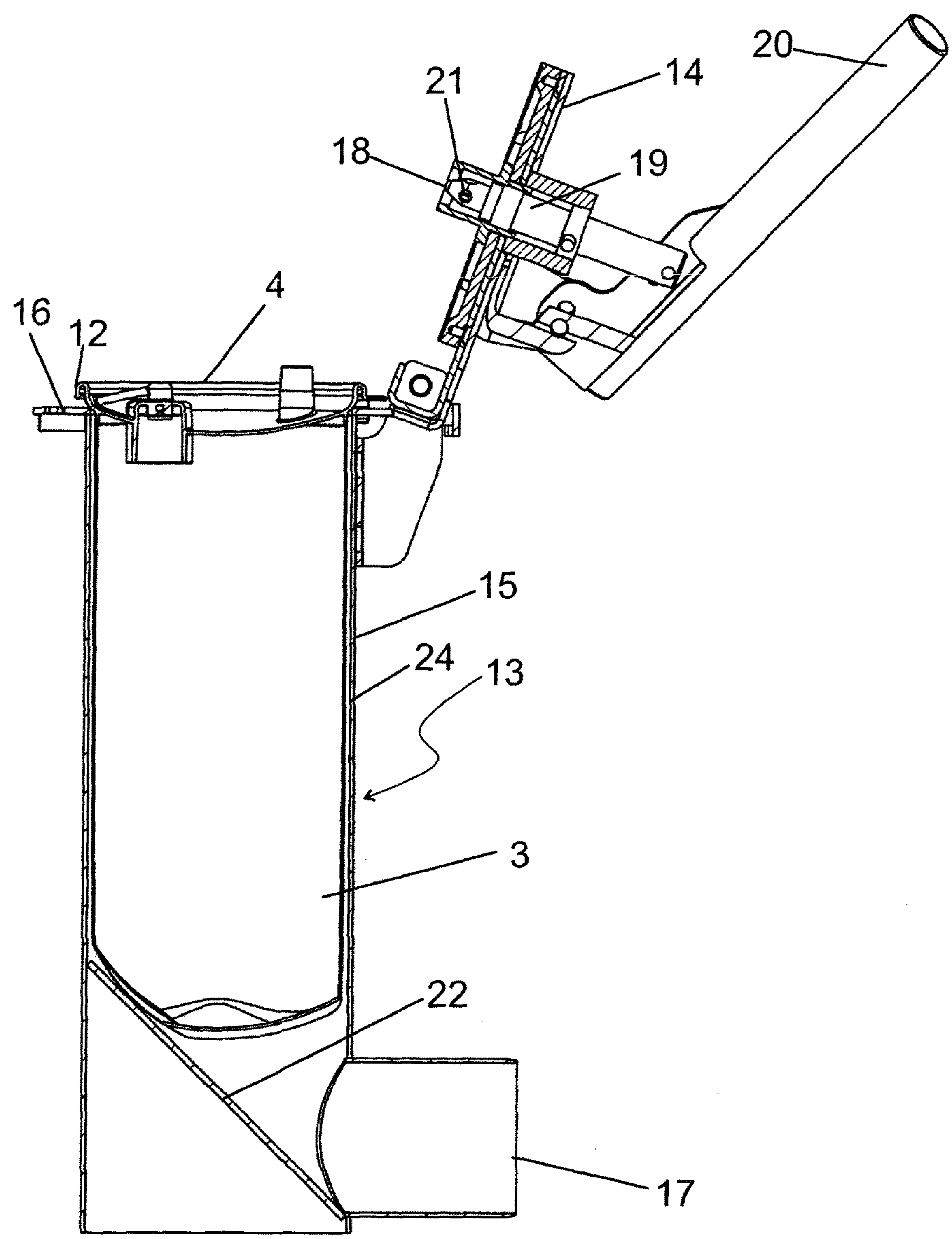
FIGS. 3 to 6 are sectional views of an emptying device of the invention.

When the suction bag 3 is emptied, it is placed into the container 15 so that the rim 12 of the lid 4 sets against the shoulder 16. The container 15 is preferably dimensioned so that its height from the bottom to the holder is greater than the length of the suction bag. Consequently, the bottom of the suction bag 3 does not touch the bottom of the container 15. In other words, the suction bag 3 hangs from the shoulder 16, as shown in FIG. 3.

Figure 4:
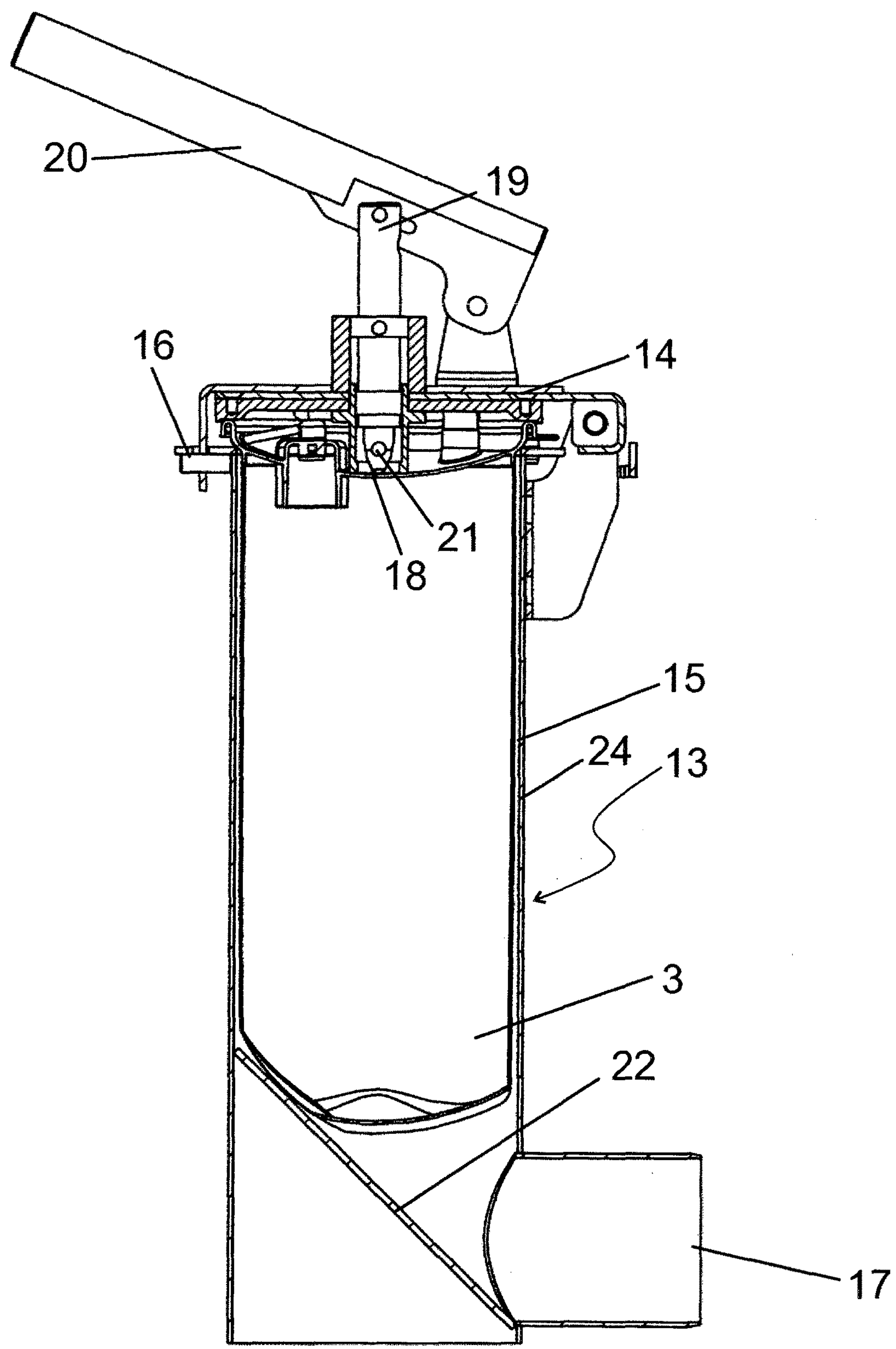
Figure 5:
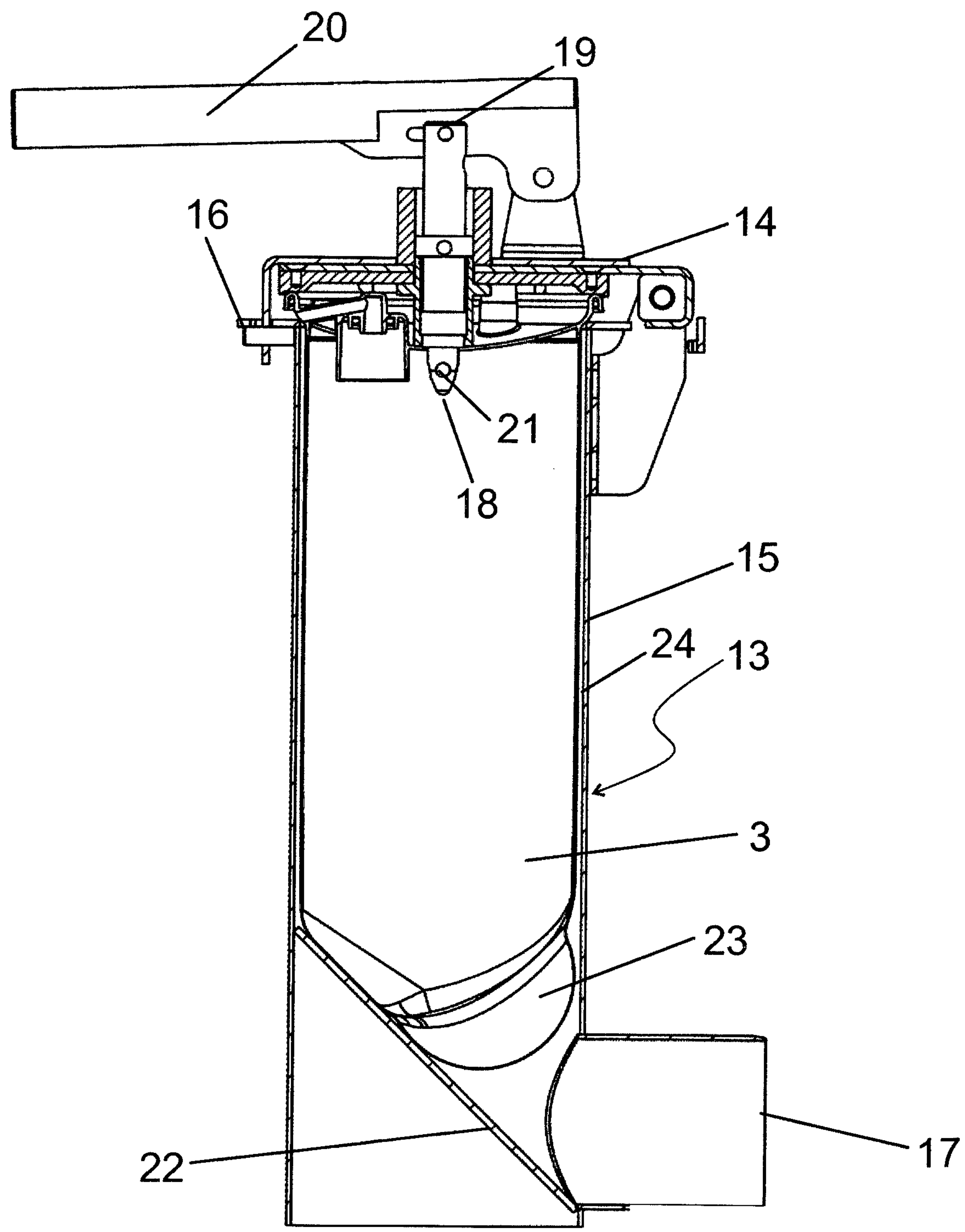

When the suction bag 3 is in place in the container 15, the lid 14 of the emptying device 13 is closed by means of a handle 20 as shown in FIG. 4. When the movement of the handle 20 is continued, the blunt conical end 18 of the cylinder 19 punctures the lid 4 of the suction bag 3 as shown in FIG. 5. The hollow cylinder 19 continues through the lid 14 and is connected on the outer surface side of the lid 14 to a source of pressurized gas or liquid. The source of pressurized gas or liquid may be a water supply network or a compressed air network, for example. The source of the pressurized gas or liquid may also be used for supplying a disinfectant or sterilizer, or a separate container for these substances may be provided, from which they are supplied into the liquid or gas flow. The opening of the source of pressurized gas or liquid may be connected to the closing of the lid 14, the closing automatically starting the gas or liquid flow through the cylinder 19 into the suction bag 3. In its simplest form the opening of the gas or liquid source may take place manually, for example by opening a water tap.

Figure 6:
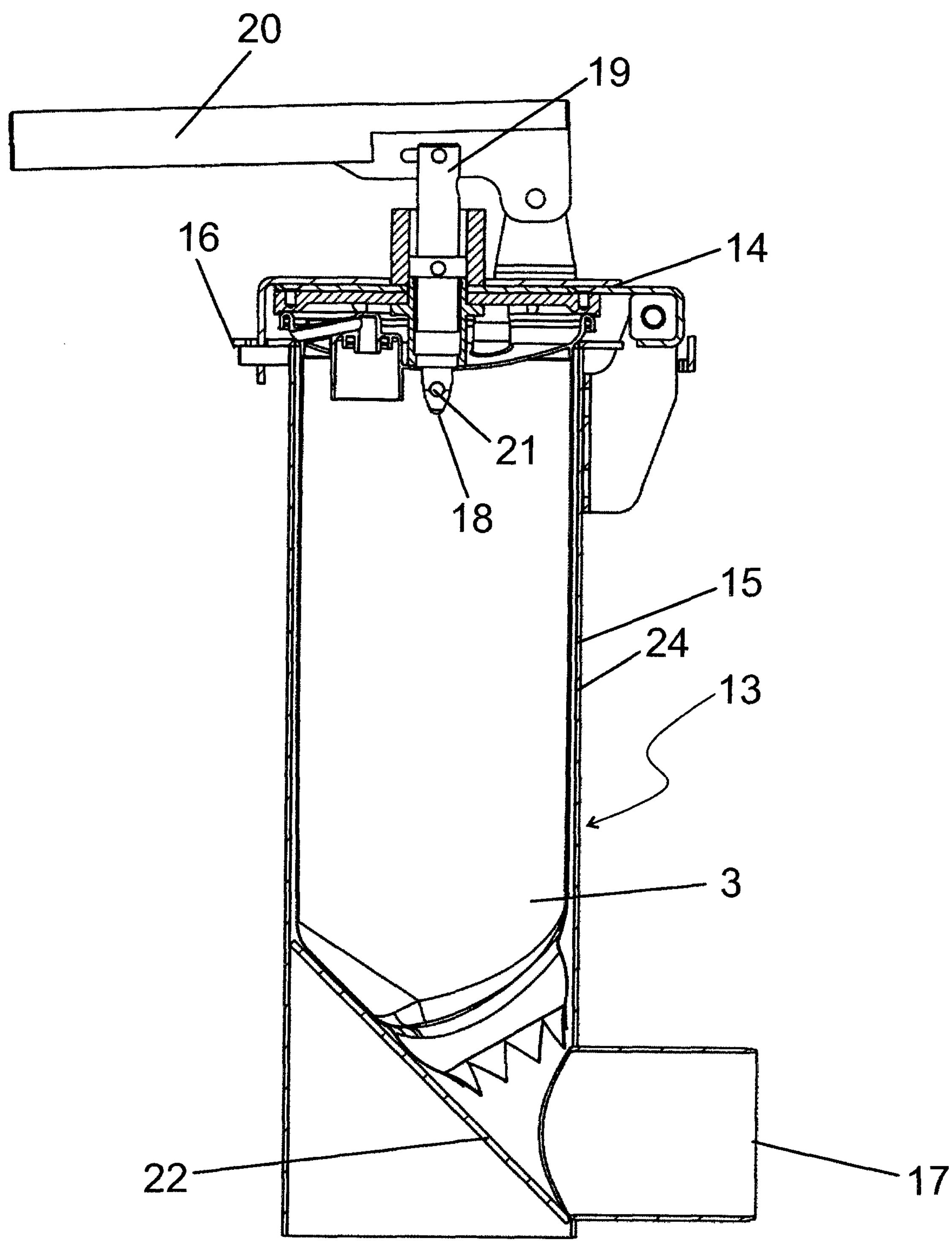

Once the pressurized gas or liquid starts to flow through the lid 4 of the suction bag 3 from the opening punctured by the conical head 18 of the cylinder 19, pressure from the inside of the suction bag 3 starts to act on the suction bag 3. The container 15 has a cylindrical jacket 24 supporting the suction bag 3 laterally. The material of the suction bag 3 starts to bulge at the bottom part of the suction bag 3, next to the seam, the bulge being marked in FIG. 5 by reference number 23. As a result of the bulging, the suction bag 3 bursts, as shown in FIG. 6. The contents of the suction bag 3 then flows out of the suction bag 3, first onto the bottom of the container 15 and then out of the container 15 through the discharge point 17. In FIG. 3 the discharge point 17 is shown merely as an opening in the jacket of the container 15, but the discharge point 17 may also be directly coupled to a sewer. There may be at least one guide surface 22 inside the container 15 to guide the flow towards the discharge point 17. When the emptying device has a guide surface 22, the guide surface 22 touches the suction bag 3 on one side of the suction bag 3, while the other side hangs free. The opening in the jacket functions well for example when the entire emptying device 13 is placed into a wash basin with a sewer. The gas or liquid continues to flow through the hollow cylinder 19, and the gas or liquid flow rinses the inside of the suction bag 3. The suction bag 3 is thus emptied completely and the rinsing ensures that the inside of the suction bag 3 is entirely clean because the gas or liquid flows through the entire suction bag 3 and through the hole formed to the bottom of the suction bag 3 as a result of the bulging.

After the rinsing has continued for a sufficient amount of time, the gas or fluid flow is cut off or the flow shuts off automatically e.g. when the cover 14 of the emptying device 13 is opened. The rinsed suction bag 3 may then be removed from the emptying device 13 and taken to waste disposal.

It will be apparent to a person skilled in the art that as technology advances, the basic idea of the invention may be implemented in many different ways. In this application the jacket of the emptying device is described as being cylindrical, but the jacket may equally well have some other shape. The cross-section of the jacket may be oval or a polygon, for example. The main thing is that the jacket supports the suction bag laterally sufficiently close to the outer surface of the suction bag. The invention and its embodiments are thus not restricted to the examples described above but may vary within the scope of the claims.

The invention claimed is:

1. An emptying device for a suction bag having a bag lid and a bag portion coupled to the bag lid, the device comprising:

a container adapted to receive the suction bag, the container includes:

a container lid including a puncture mechanism that is adapted to puncture the bag lid and supply a pressurized liquid or gas into the suction bag to cause the bag portion to burst and the suction bag to be emptied;

a discharge point for removal of contents of the suction bag;

a holder for suspending the suction bag by the bag lid; and a jacket for laterally supporting the suction bag.

2. The device as claimed in claim 1, wherein the jacket is an inner wall of the container.

3. The device as claimed in claim 1, wherein the jacket is a separate structural part inside the container.

4. An assembly comprising:

a suction bag including a bag lid and a bag portion coupled to the bag lid; and a suction bag emptying device including:

a container with a discharge point for removal of contents in the suction bag, and a container lid including a puncture mechanism that is adapted to puncture the bag lid and supply a pressurized liquid or gas into the suction bag to cause the bag portion to burst;

a holder for suspending the suction bag by the bag lid, the container having a height from a bottom of the holder that is greater than a length of the suction bag; and a jacket for laterally supporting the suction bag, wherein the jacket surrounds a side of the bag portion.

5. The assembly as claimed in claim 4, wherein the jacket is an inner wall of the container.

6. The assembly as claimed in claim 4, wherein the jacket is a separate structural part inside the container.

7. A method for emptying a suction bag having a bag lid and a bag portion coupled to the bag lid, the method comprising:

suspending the suction bag containing liquid by the bag lid from a holder of a container that has a height from a bottom to the holder that is greater than a length of the suction bag, wherein the container includes:

a discharge point for removal of contents in the suction bag;

a container lid including a puncture mechanism that punctures the bag lid and is adapted to supply a pressurized liquid or gas into the suction bag; and a jacket for laterally supporting the suction bag;

closing the container lid in order to puncture the bag lid;

supplying the pressurized liquid or gas into the suction bag to cause the bag portion to burst and the liquid to be emptied from the suction bag;

shutting off the supply of the pressurized liquid or gas; and removing the empty suction bag from the container.

* * * * *